US012558262B2

(12) United States Patent
Bor

(10) Patent No.: US 12,558,262 B2
(45) Date of Patent: Feb. 24, 2026

(54) VISUALIZATION OF VITREOUS FLOATERS IN THE EYE

(71) Applicant: Alcon Inc., Fribourg (CH)

(72) Inventor: Zsolt Bor, San Clemente, CA (US)

(73) Assignee: Alcon Inc., Fribourg (CH)

( * ) Notice: Subject to any disclaimer, the term of this patent is extended or adjusted under 35 U.S.C. 154(b) by 646 days.

(21) Appl. No.: 17/937,696

(22) Filed: Oct. 3, 2022

(65) Prior Publication Data

US 2023/0157541 A1 May 25, 2023

Related U.S. Application Data

(60) Provisional application No. 63/297,345, filed on Jan. 7, 2022, provisional application No. 63/281,314, filed on Nov. 19, 2021.

(51) Int. Cl.
*A61F 9/008* (2006.01)
*A61B 3/135* (2006.01)

(52) U.S. Cl.
CPC .......... *A61F 9/00825* (2013.01); *A61B 3/135* (2013.01); *A61F 2009/00874* (2013.01)

(58) Field of Classification Search
None
See application file for complete search history.

(56) References Cited

U.S. PATENT DOCUMENTS 3,586,424 A * 6/1971 Schenk .................. G02B 23/00
351/218
3,780,979 A 12/1973 De Guillebon 4,357,088 A 11/1982 Pomerantzeff
4,520,824 A * 6/1985 Swaniger ............. A61B 3/0075
606/18
5,312,396 A 5/1994 Feld
(Continued)

FOREIGN PATENT DOCUMENTS

AU 2018274939 B2 6/2020
CN 210009227 U 2/2020
(Continued)

OTHER PUBLICATIONS

Meridian, Nd:YAG laser Microruptor 6, Jun. 2016 (Year: 2016).*
(Continued)

*Primary Examiner* — Carl H Layno
*Assistant Examiner* — Manolis Pahakis
(74) *Attorney, Agent, or Firm* — Patterson + Sheridan, LLP

(57) ABSTRACT

In certain embodiments, an ophthalmic surgical system for viewing an eye includes an ophthalmic microscope and a laser device. The ophthalmic microscope receives light reflected or scattered backwards from within the vitreous of the eye in order to provide an image of an object within the vitreous. The ophthalmic microscope includes a slit illumination source (which includes a light source and an optical element), a spectral filter, and oculars. The slit illumination source illuminates the eye with light, where the light source provides the light, and the optical element directs the light into the eye. The spectral filter filters out red spectral components of the light. The oculars receive the light from the eye in order to provide the image of the object. The laser device generates a laser beam to direct towards the object within the eye.

19 Claims, 4 Drawing Sheets

(56)                    References Cited

U.S. PATENT DOCUMENTS

| | | | |
|---|---|---|---|
| 5,909,270 | A | 6/1999 | Moser |
| 6,142,630 | A | 11/2000 | Koester |
| 6,283,596 | B1* | 9/2001 | Yoshimura ............. A61B 3/135 |
| | | | 351/214 |
| 6,322,556 | B1 | 11/2001 | Gwon |
| 6,789,900 | B2 | 9/2004 | Van De Velde |
| 7,374,287 | B2 | 5/2008 | Van De Velde |
| 7,510,282 | B2 | 3/2009 | Ueno |
| 7,520,613 | B2 | 4/2009 | Saito et al. |
| 7,703,922 | B2 | 4/2010 | Van De Velde |
| 7,986,463 | B2* | 7/2011 | Feklistov ............. G02B 27/141 |
| | | | 359/637 |
| 8,480,659 | B2 | 7/2013 | Frey et al. |
| 8,652,602 | B1 | 2/2014 | Dolla |
| 8,783,868 | B2 | 7/2014 | Qiu |
| 8,876,808 | B2 | 11/2014 | Feklistov et al. |
| 8,994,753 | B2 | 3/2015 | Nakano |
| 9,033,500 | B2 | 5/2015 | Utsunomiya |
| 9,603,519 | B2 | 3/2017 | Bor et al. |
| 9,675,243 | B2 | 6/2017 | Sasak et al. |
| 9,789,002 | B2 | 10/2017 | Van De Velde |
| 9,877,647 | B2* | 1/2018 | Ignotz .................. A61B 5/0071 |
| 10,130,511 | B2 | 11/2018 | Dantus |
| 10,478,342 | B2 | 11/2019 | Dick |
| 10,555,835 | B2 | 2/2020 | Schuele et al. |
| 2005/0110949 | A1* | 5/2005 | Goldfain ................ A61B 3/158 |
| | | | 351/206 |
| 2005/0134796 | A1* | 6/2005 | Zelvin ...................... A61B 3/12 |
| | | | 351/206 |
| 2007/0258094 | A1 | 11/2007 | Izatt et al. |
| 2007/0291277 | A1 | 12/2007 | Everett |
| 2009/0073384 | A1 | 3/2009 | Warden |
| 2009/0137989 | A1 | 5/2009 | Kataoka |
| 2009/0196477 | A1 | 8/2009 | Cense et al. |
| 2010/0123873 | A1 | 5/2010 | Raymond |
| 2010/0152847 | A1 | 6/2010 | Padrick |
| 2011/0077557 | A1 | 3/2011 | Wing et al. |
| 2011/0282161 | A1* | 11/2011 | Bhadri ...................... A61B 3/13 |
| | | | 600/249 |
| 2012/0050515 | A1* | 3/2012 | Shikaumi ............. A61B 3/0008 |
| | | | 348/78 |
| 2012/0281235 | A1 | 11/2012 | Murata |
| 2013/0131652 | A1 | 5/2013 | Dick |
| 2013/0173029 | A1 | 7/2013 | Caldeira et al. |
| 2014/0058367 | A1 | 2/2014 | Dantus |
| 2014/0216468 | A1 | 8/2014 | Goldshleger |
| 2014/0257257 | A1 | 9/2014 | Grant et al. |
| 2014/0268036 | A1 | 9/2014 | Ketterling et al. |
| 2014/0276674 | A1 | 9/2014 | Lee |
| 2015/0190278 | A1 | 7/2015 | Gooding |
| 2015/0297755 | A1* | 10/2015 | Telandro ............ A61K 49/0073 |
| | | | 600/431 |
| 2015/0342782 | A1 | 12/2015 | Mordaunt |
| 2016/0058617 | A1 | 3/2016 | Luttrull et al. |
| 2016/0074214 | A1 | 3/2016 | Palanker et al. |
| 2016/0074221 | A1 | 3/2016 | Tassignon et al. |
| 2016/0128561 | A1* | 5/2016 | Terasaki ................ A61B 3/152 |
| | | | 351/221 |
| 2016/0166431 | A1 | 6/2016 | Vogler et al. |
| 2016/0227999 | A1 | 8/2016 | An et al. |
| 2016/0235588 | A1 | 8/2016 | Hart et al. |
| 2016/0256324 | A1* | 9/2016 | Suzuki ............... A61F 9/00825 |
| 2016/0278629 | A1 | 9/2016 | Schuele |
| 2016/0302969 | A1 | 10/2016 | Yamamoto |
| 2017/0042419 | A1* | 2/2017 | Nakanishi ................ A61B 3/15 |
| 2017/0181625 | A1 | 6/2017 | Kawakami et al. |
| 2017/0252213 | A1 | 9/2017 | Furuuchi et al. |
| 2017/0280995 | A1* | 10/2017 | Yates ....................... A61B 3/14 |
| 2017/0326003 | A1 | 11/2017 | Schuele et al. |
| 2017/0356608 | A1* | 12/2017 | Smith .................. H01S 3/0078 |
| 2018/0028354 | A1 | 2/2018 | Heeren |
| 2018/0028355 | A1 | 2/2018 | Raksi |
| 2018/0140257 | A1 | 5/2018 | Govindjee et al. |
| 2018/0206719 | A1 | 7/2018 | Adler et al. |

| | | | |
|---|---|---|---|
| 2018/0317767 | A1 | 11/2018 | Ryan |
| 2018/0353064 | A1 | 12/2018 | Soetikno et al. |
| 2018/0368915 | A1 | 12/2018 | Xia et al. |
| 2019/0117064 | A1* | 4/2019 | Fletcher ................. A61B 3/145 |
| 2019/0159933 | A1 | 5/2019 | Romano et al. |
| 2019/0282403 | A1 | 9/2019 | Barrett et al. |
| 2019/0290124 | A1 | 9/2019 | Laforest et al. |
| 2019/0313903 | A1 | 10/2019 | Mckinnon |
| 2019/0365569 | A1 | 12/2019 | Skovgaard et al. |
| 2020/0038241 | A1 | 2/2020 | Wang et al. |
| 2020/0060873 | A1 | 2/2020 | Heeren |
| 2020/0085292 | A1 | 3/2020 | Fukuma et al. |
| 2020/0129336 | A1 | 4/2020 | Schuele et al. |
| 2020/0130103 | A1 | 4/2020 | Choi |
| 2020/0192080 | A1 | 6/2020 | Karam |
| 2020/0196853 | A1 | 6/2020 | Van Hemert et al. |
| 2020/0273218 | A1 | 8/2020 | Camino et al. |
| 2020/0397289 | A1 | 12/2020 | Ralston |
| 2020/0400422 | A1 | 12/2020 | Ralston |
| 2021/0100450 | A1 | 4/2021 | Amma |
| 2021/0186753 | A1 | 6/2021 | Al-Qaisi et al. |
| 2021/0275009 | A1 | 9/2021 | Yates |
| 2021/0378507 | A1 | 12/2021 | Wallace |
| 2021/0386586 | A1 | 12/2021 | Bor |
| 2022/0012459 | A1 | 1/2022 | Schwiegerling |
| 2022/0031511 | A1 | 2/2022 | Charles |
| 2023/0157889 | A1 | 5/2023 | Bor |
| 2024/0139033 | A1* | 5/2024 | Hacker ............... A61F 9/00825 |
| 2024/0188796 | A1* | 6/2024 | Kok ................... A61B 1/00039 |

FOREIGN PATENT DOCUMENTS

| | | | |
|---|---|---|---|
| CN | 108371542 | B | 4/2020 |
| CN | 109196333 | B | 12/2020 |
| CN | 111281651 | B | 12/2020 |
| CN | 112862782 | A | 5/2021 |
| CN | 112587302 | B | 6/2021 |
| CN | 112587304 | B | 6/2021 |
| DE | 19705044 | A1 | 8/1998 |
| DE | 102019007147 | A1 | 4/2021 |
| DE | 102019007148 | A1 | 4/2021 |
| EP | 0770370 | A2 | 2/1997 |
| EP | 1212022 | B1 | 3/2005 |
| EP | 1563785 | A1 | 8/2005 |
| EP | 1638452 | B1 | 10/2006 |
| EP | 1838212 | A1 | 10/2007 |
| EP | 2144552 | A1 | 1/2010 |
| EP | 1928297 | B1 | 11/2010 |
| EP | 2459138 | A2 | 6/2012 |
| EP | 2525706 | A2 | 11/2012 |
| EP | 2898820 | A1 | 7/2015 |
| EP | 3061429 | A1 | 8/2016 |
| EP | 2890340 | B1 | 2/2017 |
| EP | 3459487 | A1 | 3/2019 |
| EP | 3501463 | A1 | 6/2019 |
| EP | 3636137 | A1 | 4/2020 |
| EP | 3861924 | A1 | 8/2021 |
| GB | 2469249 | A | 10/2010 |
| JP | 5767014 | B2 | 6/2015 |
| JP | 2017176558 | A | 10/2017 |
| JP | 6410468 | B2 | 10/2018 |
| JP | 2018196821 | A | 12/2018 |
| JP | 2018196822 | A | 12/2018 |
| JP | 2020022569 | A | 2/2020 |
| JP | 6736304 | B2 | 7/2020 |
| JP | 6839902 | B2 | 2/2021 |
| RU | 2661016 | C1 | 7/2018 |
| RU | 2692666 | C1 | 6/2019 |
| RU | 2695629 | C1 | 7/2019 |
| RU | 2710058 | C2 | 12/2019 |
| RU | 2726468 | C1 | 7/2020 |
| WO | 9958047 | A1 | 11/1999 |
| WO | 0137769 | A1 | 5/2001 |
| WO | 0195791 | A1 | 12/2001 |
| WO | 2007059189 | A2 | 5/2007 |
| WO | 2009033110 | A2 | 3/2009 |
| WO | 2009036104 | A2 | 3/2009 |
| WO | 2009039315 | A2 | 3/2009 |
| WO | 2009059400 | A1 | 5/2009 |

(56) References Cited

FOREIGN PATENT DOCUMENTS

| WO | 2010117386 A1 | 10/2010 | | |
|----|----|----|----|----|
| WO | 2014053824 A1 | 4/2014 | | |
| WO | 2015131135 A1 | 9/2015 | | |
| WO | 2015171793 A1 | 11/2015 | | |
| WO | 2016033590 A1 | 3/2016 | | |
| WO | 2017062673 A1 | 4/2017 | | |
| WO | 2017196306 A1 | 11/2017 | | |
| WO | 2017205857 A1 | 11/2017 | | |
| WO | 2020074532 A1 | 4/2020 | | |
| WO | 2020180729 A1 | 9/2020 | | |
| WO | 2020215359 A1 | 10/2020 | | |
| WO | 2020216763 A1 | 10/2020 | | |
| WO | 2020257711 A1 | 12/2020 | | |
| WO | 2021023799 A1 | 2/2021 | | |
| WO | 2021049243 A1 | 3/2021 | | |
| WO | 2021066047 A1 | 4/2021 | | |
| WO | WO-2021069168 A1 * | 4/2021 | ............ | A61F 9/008 |
| WO | 2021092211 A1 | 5/2021 | | |
| WO | 2021183637 A1 | 9/2021 | | |
| WO | 2022149028 A1 | 7/2022 | | |
| WO | 2023089416 A1 | 5/2023 | | |
| WO | 2023089459 A1 | 5/2023 | | |
| WO | 2023097391 A1 | 6/2023 | | |

OTHER PUBLICATIONS

Raul Martin, Cornea and anterior eye assessment with slit lamp biomicroscopy, specular microscopy, confocal microscopy, and ultrasound biomicroscopy, Indian Journal of Ophthalmology (Year: 2018).*

Blake F. Webb, et al.; "Prevalence of vitreous floaters in a community sample of smartphone users"; Internat'l Journal of Ophthalmology; Jun. 18, 2013; pp. 402-405; 6(3); PMC/ US National Library of Medicine National Institutes of Health.

Chirag P. Shah, et al., YAG Laser Vitreolysis vs Sham YAG Vitreolysis for Symptomatic Vitreous Floaters A Randomized Clinical Trial, JAMA Ophthalmology, Sep. 2017, 918-923, 135-9.

ELLEX Website, Treatment Guidelines—Laser Floater Removal; 2016, Ellex Medical Pty Ltd. E&OE. VB0002E, downloaded Apr. 20, 2017.

Felix Sauvage et al: "Photoablation of Human Vitreous Opacities by Light—Induced Vapor Nanobubbles", ACS Nano, vol. 13, No. 7, Jul. 9, 2019, pp. 8401-8416.

Kim Jihwan et al. "Nonmechanical Laser Beam Steering Based on Polymer Polarization Gratings: Design Optimization and Demonstration", Journal of Lightwave Technology, vol. 33, No. 10, pp. 2068-2077, May 15, 2015.

Michael J. Escuti, et al., "Geometric-Phase Holograms", Optics & Photonics News, pp. 22-29, Feb. 2016.

Milston Rebecca et al: "Vitreous floaters: Etiology, diagnostics, and management", Survey of Ophthalmology, vol. 61, No. 2, Mar. 1, 2016, pp. 211-227.

Nicusor Iftimia et al: "Hybrid retinal imaginer using line-scanning laser ophthalmoscopy and spectral domain optical coherence tomography", Optics Express, vol. 14, No. 26, Dec. 22, 2006.

Reece Bergstrom, et al., Vitreous Floaters, National Center for Biotechnology Information, May 21, 2020, 4 pages, Bookshelf ID NBK470420, StatPearls Publishing LLC, online.

Wikipedia Encyclopedia, Floater, Wikipedia Encyclopedia, Mar. 29, 2021, online: https://en.wikipedia.org/wiki/floater?wprov=sfti 1.

Zhang Yunbo et al: "Parallel large-range scanning confocal microscope based on a digital micromirror device", Optik vol. 124, No. 13 (2013), Aug. 4, 2012, pp. 1585-1588.

Adrian G.H. Podoleanu et al., Combined optical coherence tomograph and scanning laser ophthalmoscope mi nije dostupan besplatno., Electronics Letters, 34 (11), 1998.

Chi-Hung Lee, et al., Imaging vitreous floaters and cataracts with optical simulations, Optik, 194, 1-9, 2019.

Christy K. Sheehy et al., High-speed, image-based eye tracking with a scanning laser ophthalmoscope, Biomedical Optics Express, vol. 3, No. 10, 2012.

D. H. Kelly, "Retinal Inhomogeneity. II. Spatial Summation," J. Opt. Soc. Am., pp. 114-119, vol. 1, No. 1 (Jan. 1984).

D. H. Kelly, "Retinal Inhomogeneity. III. Circular-Retina Theory," D.H. Kelly, J. Opt. Soc. Am., pp. 810-819, vol. 2, No. 6 (Jun. 1985).

D.H. Kelly, "Visual Processing of Moving Stimuli," J. Opt. Soc. Am., pp. 216-225, vol. 2, No. 2 (Feb. 1985).

D.H. Kelly,, "Motion and Vision. II. Stabilized Spatio-Temporal Threshold Surface," J. Opt. Soc. Am., pp. 1340-1349, vol. 69, No. 10 (Oct. 1979).

D.H.Kelly, "Retinal Inhomogeneity. I. Spatiotemporal Contrast Sensitivity," J. Opt. Sec. Am., pp. 107-113, vol. 1, No. 1 (Jan. 1984).

Mojana F. et al.. Observations by spectral-domain optical coherence tomography combined with simultaneous scanning laser ophthalmoscopy: imaging of the vitreous, American Journal of Ophthalmol. Apr. 2010;149(4):641-650.

Nidek, Scanning Laser Ophthalmoscope Mirante SLO/OCT Mirante SLO, https://www.nidek-intl.com/product/ophthaloptom/diagnostic/dia_retina/mirante.htm.

Peter G. J. Barten, "Contrast Sensitivity of the Human Eye and its Effects on Image Quality," Chapter 3, pp. 27-40, Model for the spatial contrast sensitivity of the eye, (1999).

Pointer, J. S., & Hess, R. F. "The contrast sensitivity gradient across the human visual field: With emphasis on the low spatial frequency range,", R. F. Vision Research, 29(9), 1133-1151 (1989).

Sebag J et al., Vitreous and Vitreoretinal Interface, Ch. 21, 2015.

Sebag J., Vitreous and Vision Degrading Myodesopsia. Progress in Retinal and Eye Research Nov. 2020;79.

T Ivanova et al., Vitrectomy for primary symptomatic vitreous opacities: an evidence-based review, Eye (Lond) May 2016;30(5):645-55.

Teri T Kleinberg et al., Vitreous substitutes: a comprehensive review, Survey of Ophthalmology, 56 (4), 2011.

Damodaran et al., "Digital micromirror device based ophthalmoscope with concentric circle scanning", 2017, pp. 2766-2780, vol. 8, No. 5, Biomedical Optics Express.

Fischer et al., "Scanning Laser Ophthalmoscopy (SLO)", In: Bille JF, editor. High Resolution Imaging in Microscopy and Ophthalmology: New Frontiers in Biomedical Optics [Internet], Aug. 14, 2019, accessed on Jan. 30, 2023 from https://www.ncbi.nlm.nih.gov/books/NBK554043, Springer.

Ginner et al., "Wide-Field OCT Angiography at 400 KHz Utilizing Spectral Splitting", Photonics, Oct. 23, 2014, pp. 369-379, vol. 1, No. 4.

Heidelberg Engineering Gmbh, "Spectralis. Hardware Operating Instructions," Version 001, Aug. 2007.

Heidelberg Engineering, "SPECTRALIS. Multimodal Imaging Platform Optimized for the Posterior Segment", accessed on Jan. 30, 2023 from https://business-lounge.heidelbergengineering.com/us/en/products/spectralis/spectralis/.

Hofer et al., "Dispersion encoded full range frequency domain optical coherence tomography", Jan. 5, 2009, pp. 7-24, vol. 17, No. 1, Optics Express, US.

Hofer et al., "Fast dispersion encoded full range optical coherence tomography for retinal imaging at 800 nm and 1060 nm", Mar. 1, 2010, pp. 4898-4919, vol. 18, No. 5, Optics Express.

Leitgeb et al., "Complex ambiguity-free Fourier domain optical coherence tomography through transverse scanning", 2007, pp. 3453-3455, vol. 32, Optics Letters.

Li et al., "DMD-based three-dimensional chromatic confocal microscopy", 2020, pp. 4349-4356, vol. 59, No. 14, Applied Optics.

Martial et al., "Programmable Illumination and High-Speed, Multi-Wavelength, Confocal Microscopy Using a Digital Micromirror", Aug. 2012, e43942, vol. 7, No. 8, Plos One.

Reznicek Lukas et al., "Wide-Field Megahertz OCT Imaging of Patients with Diabetic Retinopathy", Journal of Diabetes Research, 2015, 5 pages.

Ruggeri et al., "Imaging and full-length biometry of the eye during accommodation using spectral domain OCT with an optical switch", Jul. 1, 2012, pp. 1506-1520, vol. 3, No. 7, Biomedical Optics Express.

(56)             References Cited

OTHER PUBLICATIONS

Sarunic et al., "Instantaneous complex conjugate resolved spectral domain and swept-source OCT using 3×3 fiber couplers", Feb. 2005, pp. 957-967, vol. 13, No. 3, Optics Express.

Shields et al., "Wide-angle Imaging of the Ocular Fundus", Review of the Ophthalmology, Feb. 15, 2003.

Singh, "Lasers Take Aim At Floaters", Ophthalmology Management, Jul. 1, 2019, pp. 38, 40-42, 59, vol. 23.

Singh, "Modern vitreolysis—YAG laser treatment now a real solution for the treatment of symptomatic floaters", Survey of Ophthalmology, Mar. 3, 2020, pp. 581-591, vol. 65, No. 5.

SunLED, NanoPoint-0201 Series LEDs, published Feb. 15, 2016, www.SunLEDusa.com.

Volk Optical, "Volk Idrees Mid-Vitreous Lens", Dec. 20, 2020, accessed on Dec. 20, 2020 from https://www.volk.com/...s?pr_prod_strat=collection_fallback&pr_rec_pid=4513049018402&or_ref_pid=4513048952866pr_seq=uniform.

Volk Optical, "Volk Singh Mid-Vitreous Lens", Dec. 20, 2020, accessed on Dec. 20, 2020 from https://www.volk.com/products/singh-mid-vitreous-vitreous-slit-lamp-lens?_pos=3&amp;amp;_sid=b50c0674f&amp;_ss=r.

Wang et al., "In vivo full range complex Fourier domain optical coherence tomography", Jan. 30, 2007, 054103, vol. 90, Applied Physics Letters.

Wojtkowski et al., "Full range complex spectral optical coherence tomography technique in eye imaging", 2002, pp. 1415-1417, vol. 27, No. 16, Optics Letters.

Yasuno et al., "Simultaneous B-M-mode scanning method for real-time full-range Fourier domain optical coherence tomography", 2006, pp. 1861-1865, vol. 45, No. 8, Applied Optics.

Zhang et al., Removal of a mirror image and enhancement of the signal-to-noise ratio in Fourier-domain optical coherence tomography using an electro-optic phase modulator, Jan. 15, 2005, vol. 30, No. 2, Optics Letters.

Zhou et al., "Dual channel dual focus optical coherence tomography for imaging accommodation of the eye", May 25, 2009, pp. 8947-8955, vol. 17, No. 11, Optics Express.

* cited by examiner

GRAPH
80

VISUALIZATION OF VITREOUS FLOATERS IN THE EYE

TECHNICAL FIELD

The present disclosure relates generally to ophthalmic surgical systems, and more particularly to improved visualization of vitreous floaters in the eye.

BACKGROUND

During ophthalmic laser surgery, a surgeon needs to visualize features within the eye. For example, in laser vitreolysis, a surgeon directs a laser beam towards vitreous floaters in order to remove the floaters. Eye floaters are clumps of collagen proteins that form in the vitreous. These clumps disturb vision with moving shadows and distortions, and sometimes they block vision. The laser beam disintegrates the floaters, thus improving vision. However, a surgeon must be able to see the floaters in order to direct the laser beam at the floaters.

BRIEF SUMMARY

In certain embodiments, an ophthalmic surgical system for viewing an eye includes an ophthalmic microscope and a laser device. The ophthalmic microscope receives light reflected or scattered backwards from within the vitreous of the eye in order to provide an image of an object within the vitreous. The ophthalmic microscope includes a slit illumination source (which includes a light source and an optical element), a spectral filter, and oculars. The slit illumination source illuminates the eye with light, where the light source provides the light, and the optical element directs the light into the eye. The spectral filter filters out red spectral components of the light. The oculars receive the light from the eye in order to provide the image of the object. The laser device generates a laser beam to direct towards the object within the eye.

Embodiments may include none, one, some, or all of the following features:

The spectral filter is disposed between the eye and the oculars and filters out the red spectral components of the light from the eye. The spectral filter may be disposed between a mirror and the oculars, where the mirror directs light from the eye to the oculars, and directs the laser beam towards the object within the eye.

The spectral filter is disposed between the light source and the eye and filters out the red spectral components of the light directed towards the eye.

The filtered-out red spectral components has wavelengths of 580 to 1000 nanometers.

The filtered-out red spectral components has wavelengths of wavelengths of 580 to 750 nanometers.

The slit illumination source further includes a linear polarizer that linearly polarizes the light to yield the light linearly polarized at a first axis. The ophthalmic surgical system further includes a crossed polarizer that cross polarizes the light reflected or scattered backwards from the eye to yield the light crossed polarized at a second axis substantially orthogonal to the first axis. The oculars receive the light crossed polarized at the second axis in order to provide the image of the object.

In certain embodiments, an ophthalmic surgical system for viewing an eye includes an ophthalmic microscope and a laser device. The ophthalmic microscope receives light reflected or scattered backwards from within the vitreous of the eye in order to provide an image of an object within the vitreous. The ophthalmic microscope includes a slit illumination source (which includes a light source, a linear polarizer, and an optical element), a crossed polarizer, and oculars. The slit illumination source illuminates the eye with light, where the light source provides the light, the linear polarizer linearly polarizes the light to yield the light linearly polarized at a first axis, and the optical element directs the light into the eye. The crossed polarizer cross polarizes the light reflected or scattered backwards from the eye to yield the light crossed polarized at a second axis substantially orthogonal to the first axis. The oculars receive the light crossed polarized at the second axis in order to provide the image of the object. The laser device generates a laser beam to direct towards the object within the eye.

Embodiments may include none, one, some, or all of the following features:

The linear polarizer is a sheet polarizer or a dielectric polarizer.

The crossed polarizer is a sheet polarizer or a dielectric polarizer.

The ophthalmic system further includes a spectral filter that filters out red spectral components of the light.

In certain embodiments, an ophthalmic surgical system for viewing an eye includes an ophthalmic microscope and a laser device. The ophthalmic microscope receives light reflected or scattered backwards from within the vitreous of the eye in order to provide an image of an object within the vitreous. The ophthalmic microscope includes a slit illumination source (which includes a light source, a linear polarizer, and an optical element), a spectral filter, a crossed polarizer, and oculars. The slit illumination source illuminates the eye with light, where the light source provides the light, the linear polarizer linearly polarizes the light to yield the light linearly polarized at a first axis, and the optical element directs the light into the eye. The spectral filter filters out red spectral components of the light. The crossed polarizer cross polarizes the light reflected or scattered backwards from the eye to yield the light crossed polarized at a second axis substantially orthogonal to the first axis. The oculars receive the light crossed polarized at the second axis in order to provide the image of the object. The laser device generates a laser beam to direct towards the object within the eye.

Embodiments may include none, one, some, or all of the following features:

The spectral filter is disposed between the eye and the oculars and filters out the red spectral components of the light from the eye. The spectral filter may be disposed between a mirror and the oculars, where the mirror directs light from the eye to the oculars, and directs the laser beam towards the object within the eye.

The spectral filter is disposed between the light source and the eye and filters out the red spectral components of the light directed towards the eye.

The filtered-out red spectral components has wavelengths of 580 to 1000 nanometers.

The filtered-out red spectral components has wavelengths of wavelengths of 580 to 750 nanometers.

The linear polarizer is a sheet polarizer or a dielectric polarizer.

The crossed polarizer is a sheet polarizer or a dielectric polarizer.

In certain embodiments, an ophthalmic surgical system for viewing an eye includes an ophthalmic microscope and a laser device. The ophthalmic microscope receives light reflected or scattered backwards from within the vitreous of the eye in order to provide an image of an object within the vitreous. The ophthalmic microscope includes a slit illumination source (which includes a light source, a linear polarizer, and an optical element), a spectral filter, a crossed polarizer, a mirror, and oculars. The slit illumination source illuminates the eye with light, where the light source provides the light, the linear polarizer linearly polarizes the light to yield the light linearly polarized at a first axis, and the optical element directs the light into the eye. The linear polarizer is a sheet polarizer or a dielectric polarizer. The spectral filter filters out red spectral components of the light having wavelengths of 580 to 750 nanometers. The spectral filter is disposed between the mirror and the oculars or between the light source and the eye. The crossed polarizer cross polarizes the light reflected or scattered backwards from the eye to yield the light crossed polarized at a second axis substantially orthogonal to the first axis. The crossed polarizer is a sheet polarizer or a dielectric polarizer. The mirror directs light from the eye to the oculars and directs a laser beam towards the object within the eye. The oculars receive the light crossed polarized at the second axis in order to provide the image of the object. The laser device generates a laser beam to direct towards the object within the eye.

DESCRIPTION OF EXAMPLE EMBODIMENTS

Figure 1:
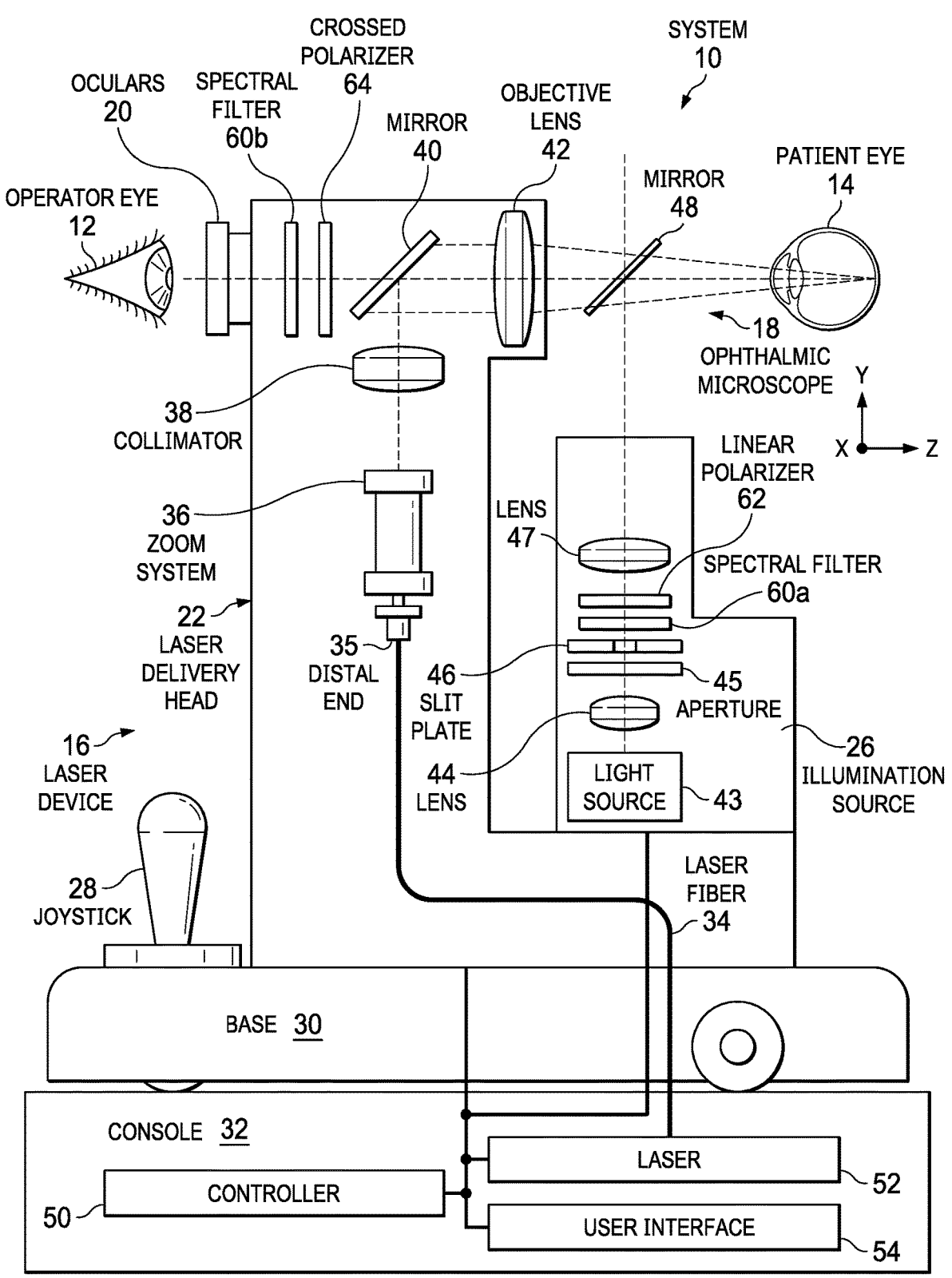
FIG. 1 illustrates an example of an ophthalmic laser system that may be used to perform laser vitreolysis on a patient eye to remove vitreous floaters, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

A surgeon should be able to see vitreous floaters in order to direct a laser beam onto the floaters. Typically, the vitreous is illuminated with a slit lamp beam. However, light reflected from a floater tends to be weaker than background light, making the floater less visible. Sources of background light include Purkinje reflections (such as P1, P2, P3, and P4 Purkinje reflections) from surfaces of the cornea and lens (e.g., natural or intraocular lens). A natural lens with a cataract may also backscatter light. The reflections and backscattering preserve the polarization of the incident slit illumination. Other sources of background light are reflections and red reflections from the retina.

Accordingly, in certain embodiments, an ophthalmic microscope uses polarization filtering to suppress the Purkinje reflections. In other embodiments, an ophthalmic microscope uses spectral filtering to suppress the red reflections. In yet other embodiments, an ophthalmic microscope uses both polarization filtering to suppress the Purkinje reflections and spectral filtering to suppress the red reflections.

FIG. 1 illustrates an example of an ophthalmic laser system 10 that an operator (with an operator eye 12) may use to perform laser vitreolysis on a patient eye 14 to remove vitreous floaters, according to certain embodiments. Vitreous floaters are microscopic collagen fibers within the vitreous that tend to clump together. These clumps scatter light and cast shadows on the retina, which appear as visual disturbances in the vision of the patient. Ophthalmic laser system 10 allows the operator to see floaters in relation to the retina and lens of the eye, and then direct a laser beam to break up the floaters.

In the example, ophthalmic laser system 10 comprises oculars 20, a laser delivery head 22, an illuminator (such as a slit illumination source 26), a positioning device (such as a joystick 28), a base 30, and a console 32, coupled as shown. Laser delivery head 22 includes a laser fiber 34, a distal end 35, a zoom system 36, a collimator 38, a mirror 40, a spectral filter 60b, a crossed polarizer 64, and an objective lens 42, coupled as shown. Slit illumination source 26 includes a light source 43, condenser lens 44, a variable aperture 45, a variable slit plate 46, a spectral filter 60a, a linear polarizer 62, a projection lens 47, and an optical element such as a mirror 48, coupled as shown. Console 32 includes a computer (such as a controller 50), a laser 52, and a user interface 54, coupled as shown. In certain embodiments, patient eye 14 has an axis (visual or optical) that defines a z-axis. Alternatively, the direction of the laser beam defines the z-axis. The z-axis defines an x-axis and a y-axis orthogonal to the z-axis. In turn, the x-axis and the y-axis define an xy-plane.

As an overview, ophthalmic laser system 10 includes a laser device 16 (e.g., laser 52, laser fiber 34, and laser delivery head 22) and an ophthalmic microscope 18 such as a slit lamp (e.g., oculars 20, objective lens 42, mirror 48, and slit illumination source 26). Operator eye 12 utilizes the optical path from oculars 20 through mirror 40, objective lens 42, and mirror 48 to view patient eye 14. A laser beam follows the laser path from laser 52 through laser delivery head 22 and mirror 48 to treat patient eye 14.

According to an overview of certain embodiments, ophthalmic microscope 18 uses polarization filtering to suppress Purkinje reflections. Purkinje reflections are reflections of objects from structures of the eye. At least four Purkinje reflections are usually visible. The first Purkinje reflection P1 is from the anterior surface of the cornea. The second Purkinje reflection P2 is from the posterior surface of the cornea. The third Purkinje reflection P3 is from the anterior surface of the lens. The fourth Purkinje reflection P4 is from the posterior surface of the lens. Unlike the others, P4 is an inverted image.

According to the overview, ophthalmic microscope 18 receives light reflected or scattered backwards from within the vitreous of eye 14 to provide an image of an object within the vitreous. Ophthalmic microscope 18 includes slit illumination source 26, crossed polarizer 64, and oculars 20. Slit illumination source 26 illuminates eye 14 with a sheet of light and includes light source 43, linear polarizer 62, and an optical element such as objective lens 42. Light source 43 provides light, and linear polarizer 62 linearly polarizes the light to yield light linearly polarized at a first axis. Objective lens 42 directs the light into eye 14. Crossed polarizer 64 cross polarizes the light from the eye to yield light crossed polarized at a second axis substantially orthogonal to the first axis. Oculars 20 receives the light crossed polarized at the second axis.

According to an overview of other embodiments, an ophthalmic microscope 18 uses spectral filtering to suppress red reflections. Red reflections are the red-orange reflections from the back of the eye. According to the overview, ophthalmic microscope 18 receives light reflected or scattered backwards from within the vitreous of eye 14 to provide an image of an object within the vitreous. Ophthalmic microscope 18 includes slit illumination source 26, spectral filter 60 (60a and/or 60b), and oculars 20. Slit illumination source 26 illuminates eye 14 with a sheet of light and includes light source 43 and an optical element such as objective lens 42. Light source 43 provides light, and objective lens 42 directs the light into eye 14. Spectral filter 60 (60a and/or 60b) filters out the red spectral components to reduce the red spectral components of the light. Spectral filter 60b may be disposed between eye 14 and oculars 20 (e.g., between mirror 40 and oculars 20), and/or spectral filter 60a may be disposed between light source 43 and eye 14. Oculars 20 receives the light crossed polarized at the second axis. According to an overview of yet other embodiments, an ophthalmic microscope uses both polarization filtering to suppress the Purkinje reflections and spectral filtering to suppress the red reflections.

In more detail, in certain embodiments, oculars 20 allow operator eye 12 to view patient eye 14. The illuminator (e.g., slit illumination source 26) of laser system 10 provides light that illuminates the surgical site of patient eye 14. In certain embodiments, slit illumination source 26 may illuminate a floater coaxially with the laser beam or at an oblique angle to the beam. Such oblique illumination reduces light scattered from the cornea and human lens and also reduces red reflex from the retina. Slit illumination source 26 includes light source 43, which emits light such as a high-intensity illumination light. Condenser lens 44 directs the light towards variable aperture 45 and variable slit plate 46. Variable aperture 45 defines the height of the light in the y-direction, and variable slit plate 43 defines the width of the light in the x-direction to form the light into a slit shape. Projection lens 47 directs the light towards prism mirror, which directs the slit of light into patient eye 14.

Spectral filter 60 filters out red spectral components to reduce the red spectral components of the light. Spectral filter 60 may be located at any suitable point of the optical path, such as at a point that is not exposed to the laser beam. In certain embodiments, spectral filter 60b is disposed between eye 14 and oculars 20 and reduces the red spectral range of the light reflected or scattered backwards from eye 14. In other embodiments, spectral filter 60a is disposed between light source 43 and eye 14 and reduces the red spectral range of the light directed towards eye 14. Spectral filter 60 may filter out any suitable red spectral components. For example, the filtered-out components may be 580 to 1000 nanometers (nm), such as 580 to 750 nanometers. Examples of spectral filter 60 includes short pass filters (used in the photographic industries) and cobalt blue filters (used in the ophthalmic industries).

Any suitable configuration of polarizers may be used. In certain embodiments, linear polarizer 62 linearly polarizes light to yield light linearly polarized at a first axis, which is directed into eye 14. Crossed polarizer 64 cross polarizes the light from the eye to yield light crossed polarized at a second axis substantially orthogonal (e.g., within 10, 5, or 3 degrees of orthogonal) to the first axis. Examples of polarizers include sheet or dielectric polarizers.

In certain embodiments, laser delivery head 22 delivers a laser beam from laser 52 of console 32 towards patient eye 14. Laser fiber 34 of delivery head 22 transports the laser beam from laser 52 to the end of fiber 34. Zoom system 36 and collimator 38 direct a parallel laser beam to mirror 40 in order to focus the laser beam onto the image plane of ophthalmic microscope 18. Zoom system 36 includes optical elements that change the spot size of the laser beam that exits fiber 34. An optical element can act on (e.g., transmit, reflect, refract, diffract, collimate, condition, shape, focus, modulate, and/or otherwise act on) light such as a laser beam. Collimator 38 collimates the laser beam, and mirror 40 directs the beam through objective lens 42, which focuses the beam. In the embodiments, mirror 40 is a dichroic mirror that is reflective for the laser beam wavelength and transmissive for visible light.

Base 30 supports laser delivery head 22 and slit illumination source 24. Joystick 28 moves base 30 in the x-, y-, and/or z-directions. Console 32 includes components that support the operation of system 10. Controller 50 of console 32 is a computer that controls of the operation of components of system 10, e.g., joystick 28, base 30, laser delivery head 22, slit illumination source 26, laser 52, and/or user interface 54. For example, in response to instructions from joystick 28, controller 50 moves the laser delivery head 22 according to the instructions. Laser 52 generates the laser beam that has a cone-shaped energy profile that focuses energy onto a point. Any suitable laser 30 may be used, e.g., a femtosecond or nanosecond laser with any suitable crystal (e.g., Nd:YAG, Erbium:YAG, Ti: Sapphire, or ruby). The laser beam may have any suitable wavelength, e.g., in a range from 500 nm to 1200 nm. User interface 54 communicates information between the operator and system 10.

Figure 2:
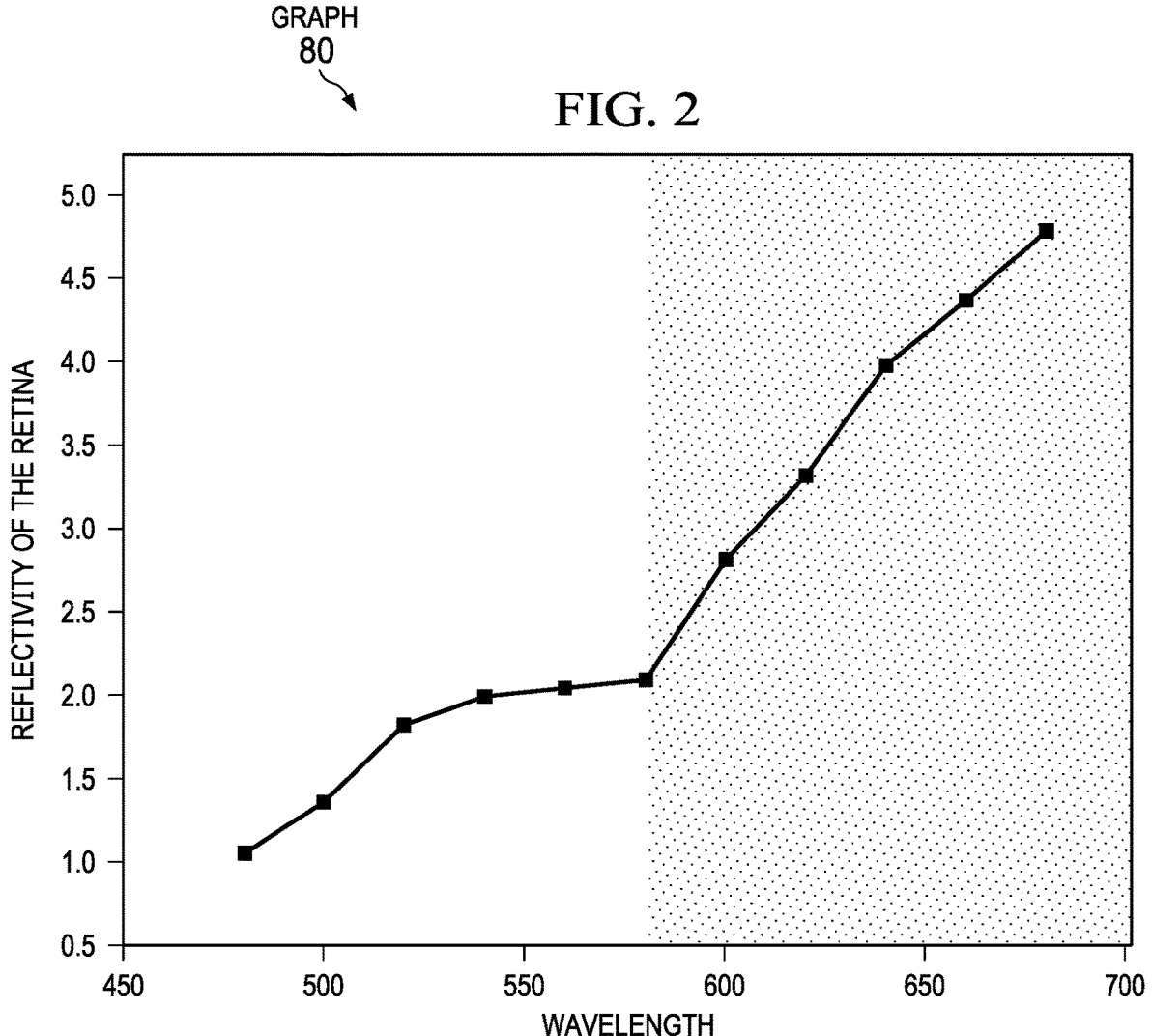
FIG. 2 is a graph illustrating the reflectivity of the retina as a function of wavelength.

FIG. 2 is a graph 80 illustrating the reflectivity of the retina as a function of wavelength. According to graph 80, the red part of the spectrum dominates the reflectivity of the retina, which causes the retina to appear to be red when viewed through a slit lamp microscope. This is called the "red reflex" of the retina. Certain embodiments described herein filter out red spectral components to reduce the red reflex.

Figure 3A:
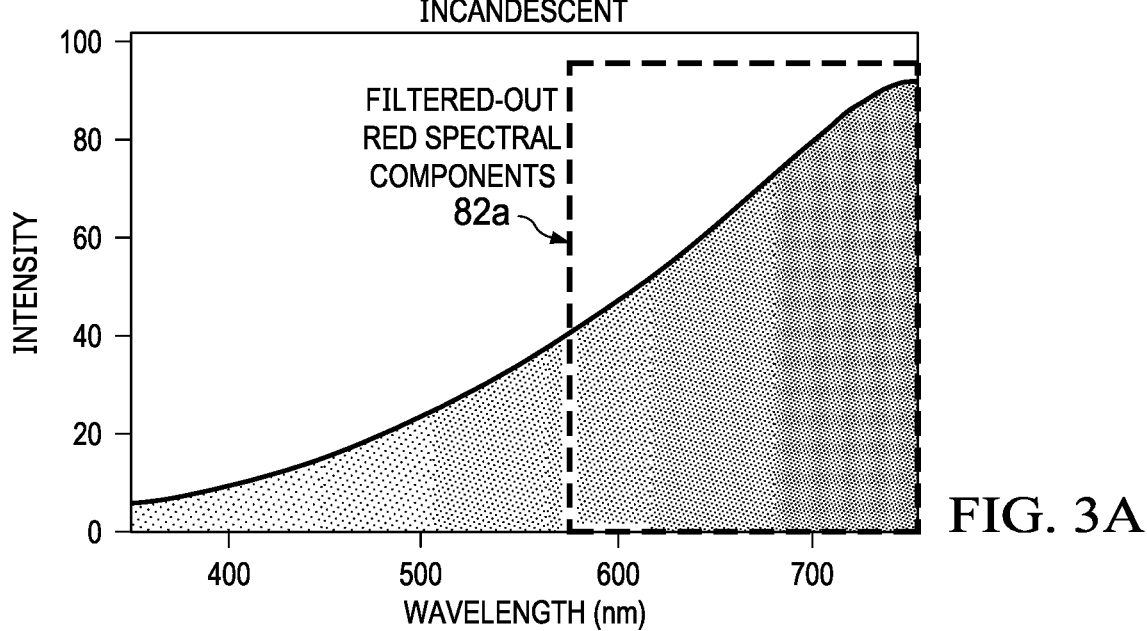
FIGS. 3A and 3B illustrate illustrates examples of red spectral components that may be filtered out by spectral filtering, according to certain embodiments.
Figure 3B:
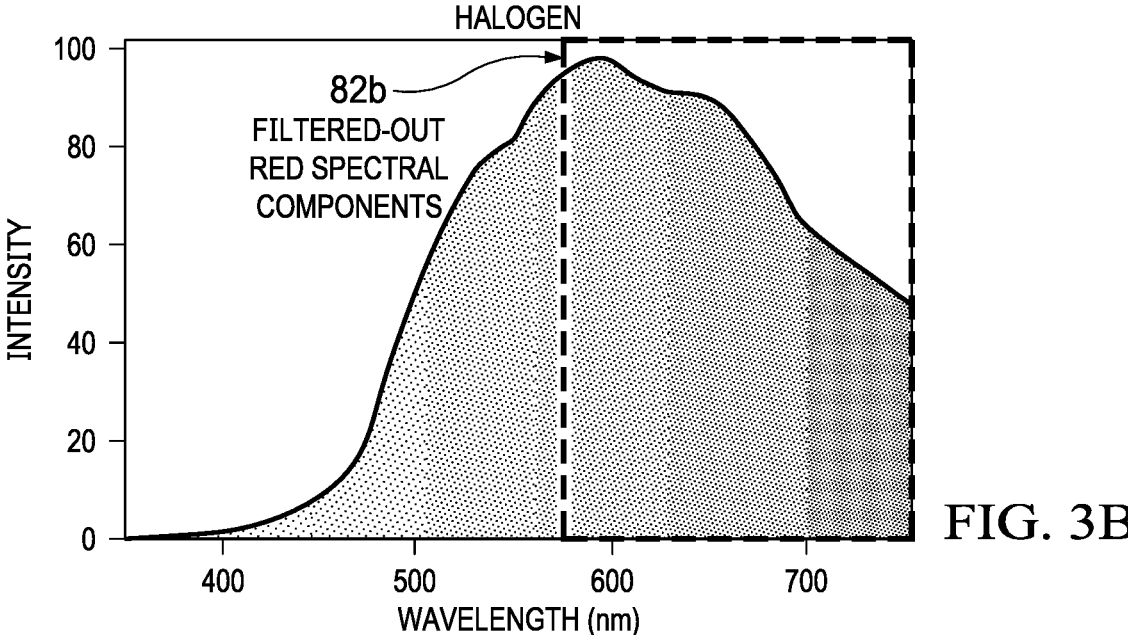

FIGS. 3A and 3B illustrate illustrates examples of red spectral components 82 (82a, 82b) that may be reduced by spectral filtering. FIG. 3A shows red spectral components 82a of 580 to 750 nm that may be used for an incandescent light source. FIG. 3B shows red spectral components 82b of 580 to 750 nm that may be used for a halogen light source or a light-emitting diode (LED) light source.

Figure 4:
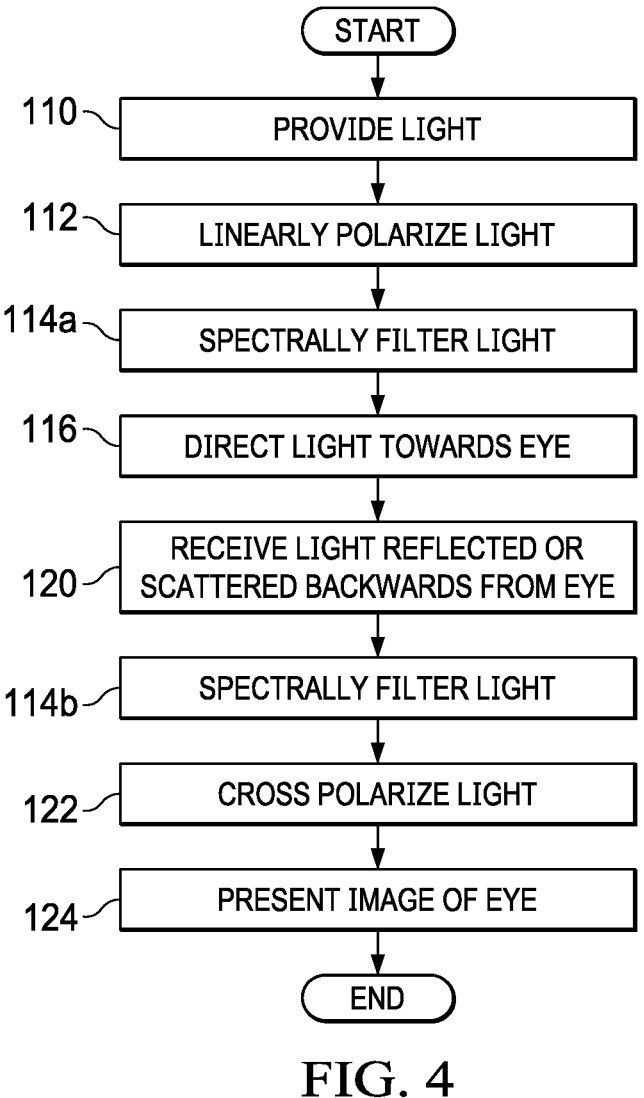
FIG. 4 illustrates an example of a method for visualizing the vitreous of a patient eye, which may be used by the system of FIG. 1, according to certain embodiments.

FIG. 4 illustrates an example of a method for visualizing the vitreous of patient eye 14, which may be used by ophthalmic laser system 10 of FIG. 1, according to certain embodiments.

The method starts at step 110, where light source 43 of an illuminator provides light. Linear polarizer 62 polarizes the light at step 112 to yield the light linearly polarized at a first axis. In certain embodiments, spectral filter 60a may filter out red spectral components at step 114a. In the embodiments, spectral filter 60a, which may be disposed between light source 43 and eye 14, reduces the red spectral range of the light directed towards eye 14. The filtered-out components may have wavelengths of 580 to 1000 nanometers, such as 580 to 750 nanometers. Mirror 23 directs light towards eye 14 at step 116.

Objective lens 42 receives light reflected or scattered backwards from eye at step 120. In certain embodiments, spectral filter 60b may filter out red spectral components at step 114b, e.g., if the red light was not previously partially or fully filtered out. In the embodiments, spectral filter 60*b,* which may be disposed between eye 14 and oculars 20 (e.g., between mirror 40 and oculars 20), reduces the red spectral components of the light from eye 14. Cross polarizer 64 cross polarizes the light at step 122 to yield the light crossed polarized at a second axis substantially orthogonal to the first axis. Oculars 20 present an image of patient eye 14 to operator eye 12 at step 124. The method then ends.

A component (such as controller 50) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic surgical system for viewing an eye, comprising:
an ophthalmic microscope configured to receive light reflected or scattered backwards from within a vitreous of the eye in order to provide an image of an object within the vitreous, the ophthalmic microscope comprising:
a slit illumination source configured to illuminate the eye with light, the slit illumination source comprising:
a light source configured to provide the light; and
an optical element configured to direct the light into the eye;
a spectral filter configured to filter out a plurality of red spectral components of the light; and
oculars configured to receive the light from the eye in order to provide the image of the object, wherein the spectral filter is disposed between the optical element and the oculars in an optical path between the oculars and the optical element, the spectral filter configured to filter out the red spectral components of the light from the eye; and
a laser device configured to generate a laser beam to direct towards the object within the eye.

2. The ophthalmic surgical system of claim 1:
further comprising a mirror configured to:
direct light from the eye to the oculars; and
direct the laser beam towards the object within the eye; and
the spectral filter disposed between the mirror and the oculars.

3. The ophthalmic surgical system of claim 1:
an additional spectral filter disposed between the light source and the eye; and
the additional spectral filter configured to filter out the red spectral components of the light directed towards the eye.

4. The ophthalmic surgical system of claim 1, the filtered-out red spectral components having wavelengths of 580 to 1000 nanometers.

5. The ophthalmic surgical system of claim 1, the filtered-out red spectral components having wavelengths of 580 to 750 nanometers.

6. The ophthalmic surgical system of claim 1:
the slit illumination source further comprising:
a linear polarizer configured to linearly polarize the light to yield the light linearly polarized at a first axis;
the ophthalmic surgical system further comprising:
a crossed polarizer configured to cross polarize the light reflected or scattered backwards from the eye to yield the light crossed polarized at a second axis orthogonal to the first axis; and
the oculars further configured to receive the light crossed polarized at the second axis in order to provide the image of the object.

7. The ophthalmic surgical system of claim 1, further comprising a mirror positioned in: (i) a first optical path from the laser device to the eye, and (ii) a second optical path from the oculars to the eye.

8. An ophthalmic surgical system for viewing an eye, comprising:

an ophthalmic microscope configured to receive light reflected or scattered backwards from within a vitreous of the eye in order to provide an image of an object within the vitreous, the ophthalmic microscope comprising:

a slit illumination source configured to illuminate the eye with light, the slit illumination source comprising:

a light source configured to provide the light;

a spectral filter configured to filter out a plurality of red spectral components of the light;

a linear polarizer configured to linearly polarize the light to yield the light linearly polarized at a first axis; and an optical element configured to direct the light into the eye;

a crossed polarizer configured to cross polarize the light reflected or scattered backwards from the eye to yield the light crossed polarized at a second axis orthogonal to the first axis; and oculars configured to receive the light crossed polarized at the second axis in order to provide the image of the object; and a laser device configured to generate a laser beam to direct towards the object within the eye.

9. The ophthalmic surgical system of claim 8, the linear polarizer comprising a sheet polarizer or a dielectric polarizer.

10. The ophthalmic surgical system of claim 8, the crossed polarizer comprising a sheet polarizer or a dielectric polarizer.

11. An ophthalmic surgical system for viewing an eye, comprising:

an ophthalmic microscope configured to receive light reflected or scattered backwards from within a vitreous of the eye in order to provide an image of an object within the vitreous, the ophthalmic microscope comprising:

a slit illumination source configured to illuminate the eye with light, the slit illumination source comprising:

a light source configured to provide the light;

a linear polarizer configured to linearly polarize the light to yield the light linearly polarized at a first axis; and an optical element configured to direct the light into the eye;

a spectral filter configured to filter out a plurality of red spectral components of the light;

a crossed polarizer configured to cross polarize the light reflected or scattered backwards from the eye to yield the light crossed polarized at a second axis substantially orthogonal to the first axis; and oculars configured to receive the light from the eye crossed polarized at the second axis in order to provide the image of the object; and a laser device configured to generate a laser beam to direct towards the object within the eye.

12. The ophthalmic surgical system of claim 11:

the spectral filter disposed between the eye and the oculars; and the spectral filter configured to filter out the red spectral components of the light from the eye.

13. The ophthalmic surgical system of claim 12: further comprising a mirror configured to:

direct light from the eye to the oculars; and direct the laser beam towards the object within the eye; and the spectral filter disposed between the mirror and the oculars.

14. The ophthalmic surgical system of claim 11:

the spectral filter disposed between the light source and the eye; and the spectral filter configured to filter out the red spectral components of the light directed towards the eye.

15. The ophthalmic surgical system of claim 11, the filtered-out red spectral components having wavelengths of 580 to 1000 nanometers.

16. The ophthalmic surgical system of claim 11, the filtered-out red spectral components having wavelengths of 580 to 750 nanometers.

17. The ophthalmic surgical system of claim 11, the linear polarizer comprising a sheet polarizer or a dielectric polarizer.

18. The ophthalmic surgical system of claim 11, the crossed polarizer comprising a sheet polarizer or a dielectric polarizer.

19. An ophthalmic surgical system for viewing an eye, comprising:

an ophthalmic microscope configured to receive light reflected or scattered backwards from within a vitreous of the eye in order to provide an image of an object within the vitreous, the ophthalmic microscope comprising:

a slit illumination source configured to illuminate the eye with light, the slit illumination source comprising:

a light source configured to provide the light;

a linear polarizer configured to linearly polarize the light to yield the light linearly polarized at a first axis, the linear polarizer comprising a sheet polarizer or a dielectric polarizer; and an optical element configured to direct the light into the eye;

a spectral filter configured to filter out a plurality of red spectral components of the light, the filtered-out red spectral components having wavelengths of 580 to 750 nanometers;

a crossed polarizer configured to cross polarize the light reflected or scattered backwards from the eye to yield the light crossed polarized at a second axis orthogonal to the first axis, the crossed polarizer comprising a sheet polarizer or a dielectric polarizer; and a mirror configured to direct light from the eye to oculars and direct a laser beam towards the object within the eye;

the oculars configured to receive the light from the eye crossed polarized at the second axis in order to provide the image of the object, the spectral filter disposed between the mirror and the oculars or between the light source and the eye; and a laser device configured to generate the laser beam to direct towards the object within the eye.

* * * * *